United States Patent
Avni et al.

(10) Patent No.: US 7,616,238 B2
(45) Date of Patent: Nov. 10, 2009

(54) METHOD FOR TIMING CONTROL OF AN IMAGE SENSOR

(75) Inventors: Dov Avni, Haifa (IL); Arkady Glukhovsky, Nesher (IL)

(73) Assignee: Given Imaging Ltd., Yoqneam (IL)

( * ) Notice: Subject to any disclaimer, the term of this patent is extended or adjusted under 35 U.S.C. 154(b) by 434 days.

(21) Appl. No.: 10/106,817

(22) Filed: Mar. 26, 2002

(65) Prior Publication Data

US 2002/0158976 A1 Oct. 31, 2002

Related U.S. Application Data

(60) Provisional application No. 60/279,406, filed on Mar. 29, 2001.

(51) Int. Cl.
H04N 9/64 (2006.01)
H04N 7/18 (2006.01)
(52) U.S. Cl. .................. 348/243; 348/65; 600/109; 374/117
(58) Field of Classification Search .................. 348/45, 348/75, 68, 243, 65; 600/109, 176; 374/117, 374/121, 141, 175
See application file for complete search history.

(56) References Cited

U.S. PATENT DOCUMENTS

| | | | |
|---|---|---|---|
| 3,971,362 A | 7/1976 | Pope et al. | |
| 4,278,077 A | 7/1981 | Mizumoto | |
| 4,646,724 A | 3/1987 | Sato et al. | |
| 4,689,621 A | 8/1987 | Kleinberg | |
| 4,844,076 A | 7/1989 | Lesho et al. | |
| 4,901,143 A * | 2/1990 | Uehara et al. | 348/65 |
| 4,957,346 A * | 9/1990 | Wood et al. | 385/117 |
| 5,010,412 A | 4/1991 | Garriss | |
| 5,279,607 A | 1/1994 | Schentag et al. | |
| 5,420,631 A | 5/1995 | Hamasaki | |
| 5,604,531 A | 2/1997 | Iddan et al. | |
| 5,819,736 A | 10/1998 | Avny et al. | |
| 5,867,045 A * | 2/1999 | Ueno et al. | 327/94 |
| 5,900,623 A * | 5/1999 | Tsang et al. | 250/208.1 |
| 5,926,214 A * | 7/1999 | Denyer et al. | 348/241 |
| 5,987,261 A * | 11/1999 | Sugahara et al. | 396/61 |
| 6,240,312 B1 * | 5/2001 | Alfano et al. | 600/476 |
| 6,276,605 B1 | 8/2001 | Olmstead et al. | |
| 6,488,390 B1 * | 12/2002 | Lebens et al. | 362/231 |
| 6,570,617 B2 * | 5/2003 | Fossum et al. | 348/308 |

(Continued)

FOREIGN PATENT DOCUMENTS

DE 34 40 177 5/1986

(Continued)

OTHER PUBLICATIONS

Supplementary European Search Report for Application No. EP 02 71 8493, Jun. 6, 2008.

(Continued)

*Primary Examiner*—Sinh Tran
*Assistant Examiner*—Hung H Lam
(74) *Attorney, Agent, or Firm*—Pearl Cohen Zedek Latzer, LLP

(57) ABSTRACT

An imaging device having an in vivo CMOS image sensor, at least one illumination source and a controller. The controller controls the illumination source to illuminate for a first period and to be shut off for a subsequent period.

10 Claims, 3 Drawing Sheets

U.S. PATENT DOCUMENTS

| | | | |
|---|---|---|---|
| 6,697,102 B1 * | 2/2004 | Olsson et al. | 348/85 |
| 6,803,947 B1 * | 10/2004 | Tomioka | 348/220.1 |
| 6,914,629 B1 * | 7/2005 | Hurwitz et al. | 348/296 |
| 6,950,131 B1 * | 9/2005 | Kleinhans et al. | 348/241 |
| 6,961,091 B1 | 11/2005 | Kubo | |
| 7,009,634 B2 * | 3/2006 | Iddan et al. | 348/76 |
| 2001/0017649 A1 * | 8/2001 | Yaron | 348/45 |
| 2001/0052930 A1 * | 12/2001 | Adair et al. | 348/65 |
| 2002/0012053 A1 * | 1/2002 | Yoshida | 348/243 |
| 2002/0057294 A1 * | 5/2002 | Ejima et al. | 345/792 |
| 2002/0134911 A1 * | 9/2002 | Zarnowski et al. | 250/208.1 |
| 2002/0161282 A1 * | 10/2002 | Fulghum | 600/160 |
| 2003/0090576 A1 * | 5/2003 | Kubota et al. | 348/220.1 |

FOREIGN PATENT DOCUMENTS

| | | |
|---|---|---|
| EP | 0773 669 A2 | 5/1997 |
| JP | 4109927 | 4/1992 |
| JP | 5015515 | 1/1993 |
| JP | 11-225996 | 8/1999 |
| JP | 11-261899 | 9/1999 |
| JP | 2000-278597 | 10/2000 |
| JP | 2001-046358 | 2/2001 |
| WO | WO 98/11816 | 3/1988 |
| WO | WO 98/37516 | 8/1998 |
| WO | WO 01/08548 | 2/2001 |
| WO | WO 01/45392 A2 | 6/2001 |

OTHER PUBLICATIONS

Office Action from Japanese Application No. 2002-578664 mailed on Mar. 4, 2008.

* cited by examiner

METHOD FOR TIMING CONTROL OF AN IMAGE SENSOR

PRIOR PROVISIONAL

The present application claims benefit from U.S. Provisional Application No. 60/279,406, filed on 29 Mar., 2001, entitled "A Method for Timing Control".

FIELD OF THE INVENTION

The present invention relates to imaging, particularly in vivo imaging, typically, by utilizing a CMOS image sensor.

BACKGROUND OF THE INVENTION

Image sensors are silicon chips that capture and measure an amount of light. A typical CMOS (complementary metal-oxide semiconductor) image sensor can perform camera functions on-chip.

Active pixel CMOS image sensors may contain a photo-detector element (a photodiode or a photogate) and an active transistor circuitry (an amplifier) integrated within the same substrate. During imaging, on chip timing and control circuits drive row and column electronics in cycles of light integration and readout followed by reset.

CMOS image sensors are typically used in low-and mid-end video cameras, for industrial purposes e.g., in robots and in quality control and for domestic use e.g., in cameras connected to personal computers.

In vivo imaging devices can utilize CMOS image sensors. For example, an in vivo imaging device may capture images of a body lumen and transmit the images to an external receiving system, while being moved along a body lumen.

SUMMARY OF THE INVENTION

The present invention provides a method for imaging, typically in vivo imaging, that enables, inter alia, the obtaining of sharp images that are not blurred, from an in vivo CMOS image sensor. Further, the method according to an embodiment of the invention may enable transmission of images from the sensor by a low power, small dimension wireless transmitter. The method, according to an embodiment of the invention may enable imaging that is not impaired by dark signal noise, even in warm environments and variable light conditions, namely, with intermittent dark periods.

As referred to herein, the term "dark period" relates to a time period in which no electrical energy, which is due to illumination, is added to the CMOS image sensor pixels, Also, as referred to herein an "in vivo CMOS image sensor" or "in vivo CMOS imager" relate to a CMOS image sensor that is obtaining images of a substantially non static scene. For example, the image sensor itself can be moving while it is obtaining images or the imaged scene may be moving (for example, a static or mobile image sensor imaging the contracting walls of the gastrointestinal (GI) tract or a static or mobile image sensor imaging a bleeding wound, etc.)

The method, according to an embodiment of the invention, includes the step of providing pixels of an in vivo CMOS image sensor with at least one period of illumination and at least one subsequent dark period.

In one embodiment, the invention comprises a method for timing control of a CMOS image sensor, Typically, the CMOS imager may be a mobile imager, for example an in vivo image sensor that is actively or passively moved through a body lumen while obtaining images of the lumen. Alternatively, the CMOS imager may be static, e.g. used for monitoring body processes in the same location. According to an embodiment of the invention the method for timing control includes the following steps: a) providing pixels in a CMOS image sensor with at least one period of illumination and at least one subsequent dark period; and b) successively reading out and resetting each pixel during the dark period. The image sensor pixel circuitry may be inactivated during the period of illumination and activated during the dark period for pixel readout.

The period of illumination and dark period together constitute the period in between frames, or the integration/readout cycle time.

Further provided, according to an embodiment of the invention, is an in vivo imaging device that includes an in vivo CMOS image sensor having pixels that that are provided with at least one period of illumination and at least one subsequent dark period.

Also provided, according to another embodiment of the invention, is an imaging device that includes a CMOS image sensor having timing circuitry that is programmed to effect successive readout and resetting of the image sensor pixels during a dark period only and to inactivate pixel circuitry during a period of illumination. Thus, by utilizing the method and device of the invention an inexpensive miniaturized, battery powered imaging apparatus is attainable. Such an apparatus may be advantageous in imaging ordinarily inaccessible or difficult to reach areas, for example, for imaging body lumens.

In one embodiment the method and device of the invention may be used in a swallowable capsule to obtain images of a large portion of the GI tract. A wireless capsule comprising the imaging device of the inventions illumination for illuminating a site of interest in the GI tract and a transmitter for transmitting images captured by the imaging device to an external receiving system, can perform as an autonomous endoscope for imaging the GI tract.

BRIEF DESCRIPTION OF THE DRAWINGS

The present invention will be understood and appreciated more fully from the following detailed description taken in conjunction with the drawings in which.

DETAILED DESCRIPTION OF THE INVENTION

Figure 1:
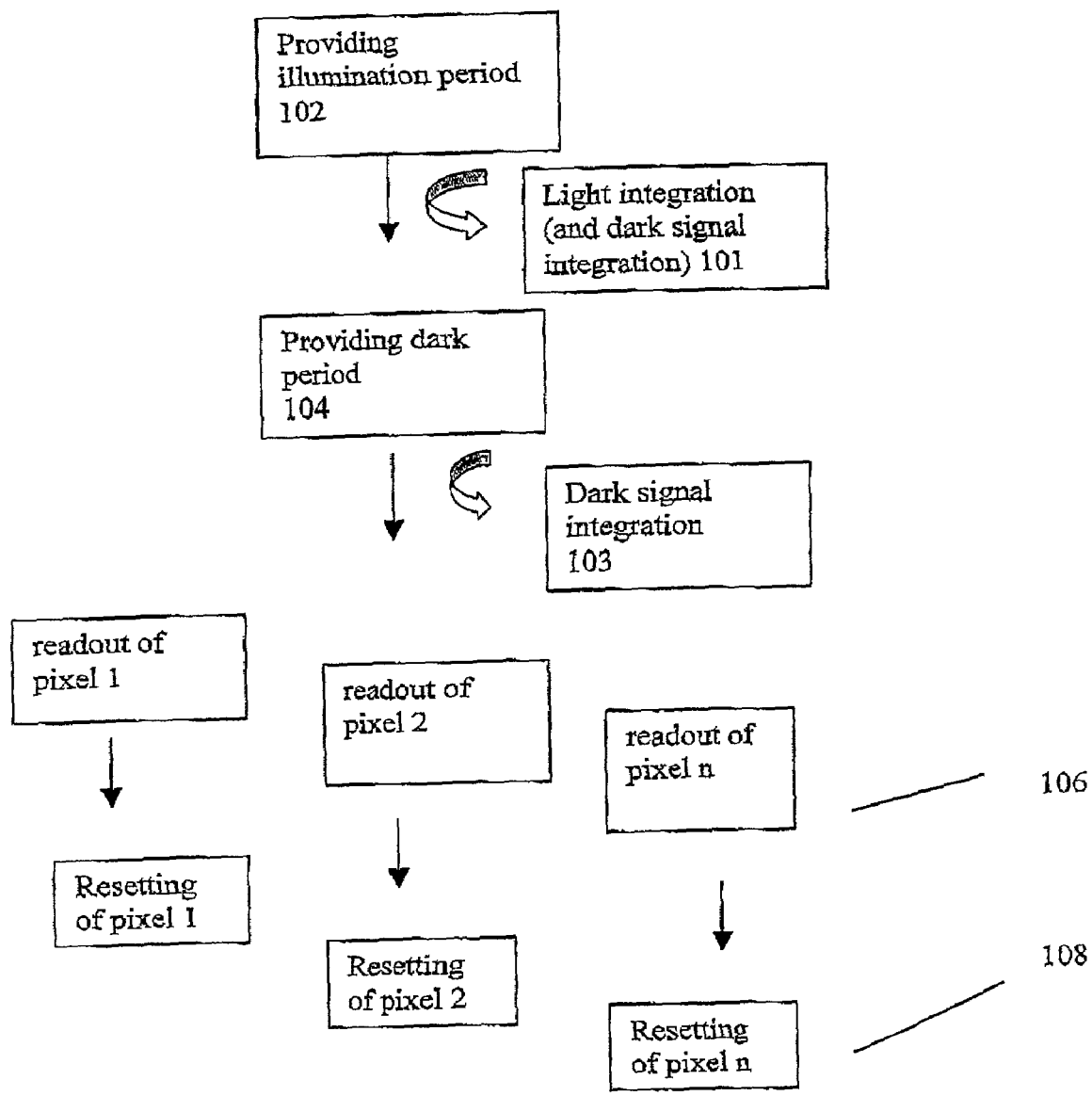
FIG. 1 is a box diagram of the method according to an embodiment of the invention.

An embodiment of the method of the present invention is schematically illustrated in FIG. 1. Referring to FIG. 1, in an in vivo CMOS image sensor having pixels, an illumination period is provided for the pixels (102), whereby light integration (and dark signal integration) takes place (101) in the pixels. Subsequently, a dark period is provided (104), e.g. by turning off the illumination or by covering the pixels so that they are unexposed to illumination. In alternate embodiments, other steps or techniques may be used according to the present invention, to provide a dark period, This sequence of steps produces one frame and may be repeated for obtaining as many frames as required. For example, the method, repeated m times, will result in m image frames.

Typically, the CMOS image sensor is mobile. An imager comprising an in vivo CMOS image sensor according to embodiments of the invention, may be a miniaturized, low powered (e.g., battery powered) imaging apparatus, optionally capable of transmitting image data to an external receiving unit. In such an imaging apparatus energy considerations (or other considerations, such as bandwidth considerations, etc.) may require obtaining a typically small number of frames per time unit. Consequently, each frame may be obtained during a typically long exposure time, in which movement of the imager or of the imaged scene will result in blurry and not sharp images. According to an embodiment of the invention, the exposure time is reduced by providing, within an integration cycle, a dark period as well as a light period. The method may further include the additional steps of successively reading out (106) and resetting (108) the pixels.

In one embodiment, for example, in an image sensor having n pixels, all n pixels are illuminated simultaneously in an illumination period (102) whereby all the pixels are exposed to the same light integration time (101), Following the illumination period (102) all n pixels are exposed to a dark period (104) in which only integration of dark signal noise occurs (103). During the dark period the pixels are successively read out (106) and reset (108); pixel 1 is read out and reset, pixel 2 is read out following readout of pixel 1 and reset and so on until pixel n is read out and reset. This sequence of steps produces one frame and may be repeated for obtaining as many frames as required. The method, repeated m times, will result in m image frames. In alternate embodiments, only a portion of the pixels may be exposed to an illumination period and other steps and sequences of steps may be used according to the present invention.

According to an embodiment of the invention, during the illumination period the underlying electronic system may be inactive while the photonic system of the pixel reacts to the illumination by light integration (dark signals are also being integrated). Typically, all the pixels are exposed to illumination for the same amount of time. Following the illumination period the pixels are exposed to a dark period (for example, either by turning off the illumination or by covering the pixels so tat they are unexposed to illumination). No light integration occurs during the dark period, however the pixels are integrating dark signal noise. During the dark period the electronic system is activated for readout and resetting of the pixels. The repetitive nature of the imager operation ensures that each pixel is exposed to the same amount of dark signal integration time (this point is further illustrated in FIG. 2).

In alternate embodiments, other sequences may be used. For example, in an alternative embodiment, the readout and reset of the pixels can be performed continuously, with no special sequence, during the exposure period. In his embodiment the exposure and illumination occur dung readout and reset of some of the pixels. Typically, these pixels are not used Her for obtaining valid image information, while all other pixels can be used for obtaining valid information.

As discussed above, providing intermittent, short periods of illumination enables the obtaining of images with less or without a blurring effect, even during movement of the image sensor or movement of the imaged scene. Readout and resetting of each pixel individually during a dark period may ensure that all the pixels are exposed to the same amount of dark signal integration. The typically equal exposure time to dark signal integration helps to ensure a consistent baseline noise for all the pixels, enabling to produce a significant signal. For example, in order to eliminate noise, a dark frame may be subtracted from every image frame. However, in an embodiment of the method of the invention, since the baseline dark signal noise remains more or less consistent, it is possible to obtain noise free image frames with out subtracting dark frames. In alternative embodiments different pixels may be exposed to different integration times. In this case the pixels may still be exposed to the same illumination period, typically resulting only in different integration time during the dark period. In another embodiment different pixels may be exposed to different illumination periods. In this case different output may be obtained from different pixels, while being exposed to the same scene. In this case a normalization algorithm may be implemented in image post-processing.

Embodiments of the method of the invention are beneficial, inter alia, for use in obtaining images from ordinarily inaccessible or difficult to reach areas, such as in miniaturized manufacturing processes, in geological surveys or in imaging in vivo. For example, embodiments of the invention may be used in a swallowable capsule to obtain images of large sections of the gastrointestinal (GI) tract as will be further described with reference to FIG. 3.

Figure 2:
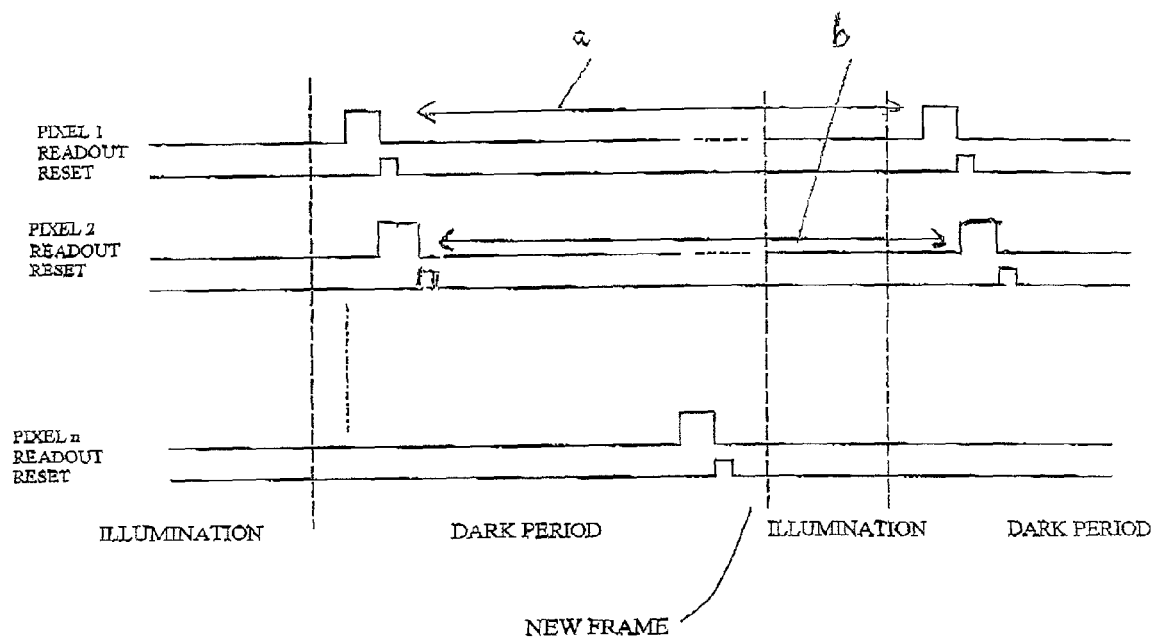
FIG. 2 shows the timing diagram for readout according to one embodiment of the invention.

The timing diagram for readout according to an embodiment of the invention is presented in FIG. 2. Referring to FIG. 2, readout of individual pixels typically begins in the dark period, directly after an illumination period. Immediately following readout of pixel 1 (line 1) pixel 1 is reset (line 2) and, simultaneously, pixel 2 is readout (line 3) and reset (line 4), and so on until pixel n, which is the last pixel in the pixel array of the image sensor, is readout and reset. In one embodiment there are, for example, 256×256 pixels in the pixel array; other dimensions may be used. The pixels are typically, but not necessarily, read out in order of their rows. Other steps or series of steps may be used, and other timing sequences may be used.

In one embodiment, a period of illumination together with the subsequent dark period define a frame. In an imaging device taking, for example, 2 frames/second the illumination period is typically 10-100 ms and the dark period is typically 400-480 ms. Other sequences and lengths of time may be used, and other readout rates may be used.

During the period of illumination light integration (and dark signal integration) may occur in all the pixels for the same amount of time. During the dark period each pixel may be exposed to dark signal integration before and after its readout and reset. Although the readout points in time are typically different for every pixel, the distance between two points of readout on a pixel is typically the same for all the pixels (e.g., distance a is equal to distance b). This helps to ensure that each pixel in the image sensor has the same amount of dark signal integration time, thereby lowering the variation in the dark signal noise generated by each pixel.

Figure 3:
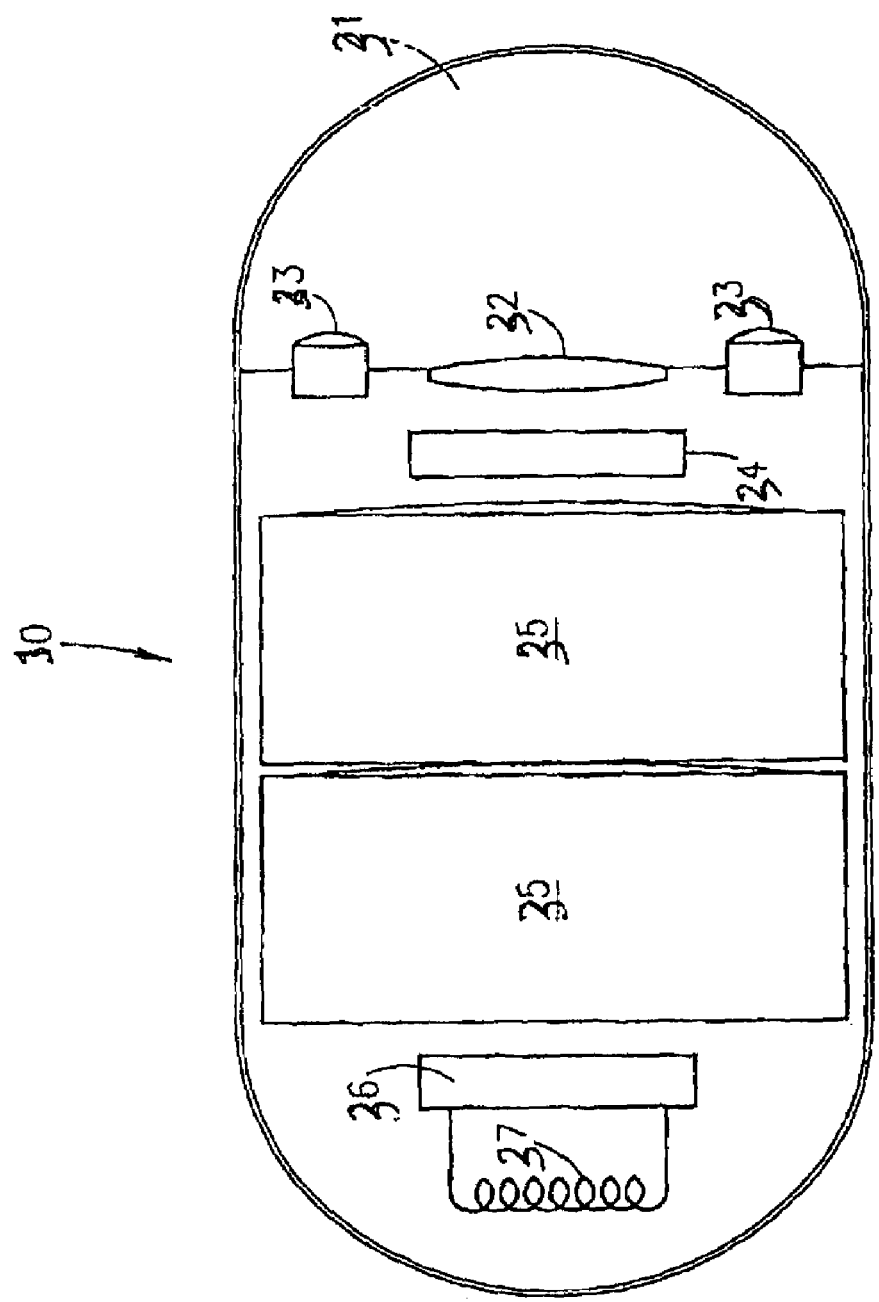
FIG. 3 is a schematic longitudinal cross section illustration of an in vivo imaging device according to an embodiment of the invention.

Reference is now made to FIG. 3, which illustrates an in vivo imaging device utilizing the method according to an embodiment of the invention. The device, which may be wireless, comprises a CMOS image sensor, an illumination source for illuminating a site of interest in vivo and a transmitter for transmitting images captured by the image sensor to an eternal receiving system. Other arrangements of components may be used, and the system and method of the present invention may be used with other devices.

Device 30 typically comprises an optical window 31 and an imaging system for obtaining images from inside a body lumen, such as the GI tract. The imaging system includes an illumination source 33, such as a white LED, a CMOS imaging camera 34, which detects the images and an optical system 32 which focuses the images onto the CMOS imaging camera 34. The illumination source 33 illuminates the inner portions of the body lumen through optical window 31.

Device 30 farther includes a transmitter 36 and an antenna 37 for transmitting the video signal of the CMOS imaging camera 34, and a power source 35, such as a silver oxide battery, that provides power to the electrical elements of the device 30.

A device that may be suitable for use with embodiments of the invention is described in WO 01/65995, which is assigned to the common assignee of the present invention and which is hereby incorporated in its entirety by reference.

Typically, the device 30 is capsule shaped, can be easily swallowed and may passively pass through the entire GI tract, pushed along by natural peristalsis. Nonetheless, it should be appreciated that the device may be of any shape suitable for being inserted into and passing through a body lumen or cavity. Furthermore, the device according to an embodiment of the invention may be attached or affixed on to an instrument that is inserted into body lumens and cavities, such as on an endoscope, laparoscope, stent, needles catheter etc.

Thus, the device may be introduced into a body lumen or cavity by swallowing, by using an endoscopic device, by surgery, etc.

The device 30 images the GI tract while being moved along by peristalsis and transmits the signals obtained on a battery powered transmitter. The transmitter 36 may be, for example, an ASIC (application specific integrated circuit) operating on a frequency shift keying (FSK), phase shift keying (PSK) or minimum shift keying (MSK) modulation system to transmit digital signals through an antenna 37 on radio frequency to an external receiving system. The transmitter 36 may include a control logic block for communicating with the imager and an illumination source power and control block for controlling the illumination. In one embodiment, the control logic block maintains a master clock, is synchronized by bit rate data and frame rate, and through a control, which may be generated by the imager, triggers the illumination source power and control block. The control logic block may further control the master clock and other imager parameters. An alternative embodiment may include a dedicated controller, which is not part of a transmitter.

The illumination source 33 of the capsule is typically programmed to illuminate short flashes of light in predetermined intervals. In between the flashes, the body lumen is dark. Typically, every flash enables acquisition and subsequent transmission of one frame.

According to one embodiment the CMOS image sensor 32 includes pixels containing a photo-detector element and readout circuitry, resetting circuitry and timing circuitry. The timing circuitry, that is coordinated with the operation of the illumination source 33, is programmed to effect successive readout and resetting of the pixels during the dark period only and to inactivate pixel circuitry during the period of illumination. Dark signal noise generated in imaging sensors increases in a temperature dependant manner. Slow sampling image sensors operating in warm environments, such as in vivo (e.g., 37° C.), have to deal with a relatively large dark signal noise component. Part of he noise cancellation processes may involve having the amplifiers of the pixel begin readout from the pixel only over an average value of dark signals. Variation in the dark signal noise generated by each pixel will cause an unsteady noise baseline, which will cause the production of a distorted image. As discussed in reference to FIG. 2, the embodiments of the invention may guaranty that each pixel in the image sensor has the same amount of dark signal integration time, thereby lowering the variation in the dark signal noise generated by each pixel.

Embodiments of the invention are typically operative at a rate of 1-10 frames per second with a CMOS image sensor having between 128×128 and 512×512 pixels, preferably 256×256 pixels, and a transmitter transmitting video signals at a range of hundreds of MHz to GHz or about 1.35 Megabit per second; other frequencies may be used. The transmission is usually to a relatively closely located to a receiving system. Thus, an embodiment of the method and device of the invention can be operable at a power input as low as 10 mW.

It will be appreciated by persons skilled in the art that the present invention is not limited to what has been particularly shown and described hereinabove. Rather the scope of the present invention is defined only by the claims which follow:

The invention claimed is:

1. A method for in vivo imaging comprising the steps of:
    illuminating with an at least one white LED a site in vivo for at least one period of illumination;
    providing pixels of an in vivo image sensor with at least one period of illumination during which the pixel circuitry is inactivated and at least one subsequent dark period with the at least one white LED turned off during which integration of dark signals occurs for each pixel for a period of time measured as time elapsed between two consecutive readout pulses applied to the pixel;
    successively reading out and then immediately resetting each pixel during the dark period to obtain an image frame; and
    eliminating dark signal noise from each image frame.

2. A method according to claim 1 wherein in vivo is in the gastrointestinal tract.

3. The method according to claim 1 wherein the step of providing pixels with at least one period of illumination and at least the one subsequent dark period is performed on all the pixels of the image sensor.

4. The method according to claim 1 wherein the step of providing pixels with at least one period of illumination and at least the one subsequent dark period is performed on 256×256 pixels.

5. The method according to claim 1 wherein the steps are repeated m times to obtain m image frames.

6. The method according to claim 1 further comprising the step of transmitting signals read out from the pixels to an external receiving system.

7. The method according to claim 6 wherein the step of transmitting signals is performed during the subsequent dark period.

8. The method according to claim 7 wherein the step of transmitting signals is preformed at a bandwidth of about 1.35 Megabit per second.

9. The method according to claim 1 wherein eliminating dark signal noise is performed by subtracting a dark frame from an image frame.

10. The method according to claim 1 wherein each pixel of the image sensor is exposed for a same amount of dark signal integration time thereby lowering variation in dark signal noise.

* * * * *

UNITED STATES PATENT AND TRADEMARK OFFICE
CERTIFICATE OF CORRECTION

PATENT NO. : 7,616,238 B2  Page 1 of 1
APPLICATION NO. : 10/106817
DATED : November 10, 2009
INVENTOR(S) : Avni et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 954 days.

Signed and Sealed this

Nineteenth Day of October, 2010

David J. Kappos
*Director of the United States Patent and Trademark Office*